US006773670B2

United States Patent
Stringer et al.

(10) Patent No.: US 6,773,670 B2
(45) Date of Patent: Aug. 10, 2004

(54) BLOOD FILTER HAVING A SENSOR FOR ACTIVE GAS REMOVAL AND METHODS OF USE

(75) Inventors: Steven K. Stringer, Santa Clara, CA (US); Kevin L. Hultquist, Mountain View, CA (US); Mehrdad Farhangnia, Sunnyvale, CA (US); Fred I. Linker, Los Altos, CA (US); Ben F. Brian, III, Menlo Park, CA (US)

(73) Assignee: CardioVention, Inc. c/o The Brenner Group, Inc., Cupertino, CA (US)

( * ) Notice: Subject to any disclaimer, the term of this patent is extended or adjusted under 35 U.S.C. 154(b) by 0 days.

(21) Appl. No.: 10/067,434

(22) Filed: Feb. 5, 2002

(65) Prior Publication Data

US 2002/0114731 A1 Aug. 22, 2002

Related U.S. Application Data

(63) Continuation-in-part of application No. 09/780,923, filed on Feb. 9, 2001.

(51) Int. Cl.⁷ .......................... A61M 1/36; A61M 32/00; B01D 59/12; B01D 26/02
(52) U.S. Cl. .......................... 422/44; 604/6.09; 604/6.1; 604/6.15; 210/349; 210/323.1; 96/6; 96/421
(58) Field of Search ...................... 422/44–48; 604/4.01, 604/5.01, 6.09, 6.1, 6.11, 6.14, 6.15; 128/DIG. 3; 261/DIG. 28, 19, 24, 26, 28–30, 83–85, 87, 106, 109–110; 210/739, 741, 348–51, 416.1, 321.6, 323.1, 383, 418, 483, 497, 501, 501.1, 501.3, 542, 321.84; 96/4–6, 10, 11, 234, 240, 243, 355, 373, 374, 155, 156, 174, 181, 244, 417, 421–22

(56) References Cited

U.S. PATENT DOCUMENTS

| 3,701,433 A | 10/1972 | Krakauer et al. |
| 3,827,562 A | 8/1974 | Esmond |
| 4,056,476 A | 11/1977 | Mouwen et al. |
| 4,087,363 A | 5/1978 | Rosemeyer et al. |

(List continued on next page.)

FOREIGN PATENT DOCUMENTS

DE          43 26 886 A1     2/1995

OTHER PUBLICATIONS

Matayoshi et al., "Development of a Completely Close Circuit Using an Air Filter in a Drainage Circuit for Minimally Invasive Cardiac Surgery," *Artificial Organs* 24(6): 454–458 (2000).

(List continued on next page.)

*Primary Examiner*—Angela D. Sykes
*Assistant Examiner*—Patricia Bianco
(74) *Attorney, Agent, or Firm*—Nicola A. Pisano, Esq.; Luce, Forward, Hamilton & Scripps, LLP

(57) ABSTRACT

Apparatus and methods for removing gas from a blood handling system. A filter apparatus for monitoring and removing gas is provided comprising of a gas removal/blood filter, a sensor to sense the presence of gas, and a valve operably coupled to the sensor to evacuate gas from the apparatus when the sensor detects an accumulation of gas. When used with a previously known blood handling system, the present filter apparatus facilitates priming and the addition of additional blood handling elements during operation of the blood handling system.

34 Claims, 4 Drawing Sheets

U.S. PATENT DOCUMENTS

| | | |
|---|---|---|
| 4,111,829 A | 9/1978 | Bimond et al. |
| 4,126,558 A | 11/1978 | Luceyk |
| 4,157,965 A | 6/1979 | Raible |
| 4,164,468 A | 8/1979 | Raible |
| 4,280,495 A | 7/1981 | Lampert |
| 4,283,289 A | 8/1981 | Meyst et al. |
| 4,319,580 A | 3/1982 | Colley et al. |
| 4,354,500 A | 10/1982 | Colley et al. |
| 4,354,501 A | 10/1982 | Colley et al. |
| 4,354,502 A | 10/1982 | Colley et al. |
| 4,401,566 A | 8/1983 | Igari et al. |
| 4,411,783 A | 10/1983 | Dickens et al. |
| 4,490,254 A | 12/1984 | Gordon et al. |
| 4,490,331 A | 12/1984 | Steg, Jr. |
| 4,493,705 A | 1/1985 | Gordon et al. |
| 4,572,724 A | 2/1986 | Rosenberg et al. |
| 4,653,577 A | 3/1987 | Noda |
| 4,662,906 A | 5/1987 | Matkovich et al. |
| 4,676,771 A | 6/1987 | Henke |
| 4,690,762 A | 9/1987 | Katsura |
| 4,698,207 A | 10/1987 | Bringham et al. |
| 4,747,826 A | 5/1988 | Sassano |
| 4,876,066 A | 10/1989 | Bringham et al. |
| 4,919,802 A | 4/1990 | Katsura |
| 4,923,438 A | 5/1990 | Vasconcellos et al. |
| 4,981,413 A | 1/1991 | Elonen et al. |
| 5,011,469 A | 4/1991 | Buckberg et al. |
| 5,017,103 A | 5/1991 | Dahl |
| 5,055,198 A | 10/1991 | Shettigar |
| 5,158,533 A | 10/1992 | Strauss et al. |
| 5,162,102 A | 11/1992 | Nogawa et al. |
| 5,188,604 A | 2/1993 | Orth |
| 5,205,153 A | 4/1993 | Hlavinka et al. |
| 5,232,437 A | 8/1993 | Lysaght et al. |
| 5,266,265 A | 11/1993 | Raible |
| 5,270,005 A | 12/1993 | Raible |
| 5,334,309 A | 8/1994 | Huggett et al. |
| 5,394,732 A | 3/1995 | Johnson et al. |
| 5,411,472 A | 5/1995 | Steg, Jr. et al. |
| 5,445,613 A | 8/1995 | Orth |
| 5,503,801 A | 4/1996 | Brugger |
| 5,514,335 A | 5/1996 | Leonard et al. |
| 5,591,251 A | 1/1997 | Brugger |
| 5,632,894 A | 5/1997 | White et al. |
| 5,634,892 A | 6/1997 | Whalen |
| 5,651,765 A | 7/1997 | Haworth et al. |
| 5,746,575 A | 5/1998 | Westphal et al. |
| 5,752,931 A | 5/1998 | Nazarian et al. |
| 5,762,684 A | 6/1998 | Hayashi et al. |
| 5,813,972 A | 9/1998 | Nazarian et al. |
| 5,823,986 A | 10/1998 | Peterson |
| 5,899,873 A | 5/1999 | Jones et al. |
| 5,997,816 A | 12/1999 | McIntosh et al. |
| 6,017,493 A | 1/2000 | Cambron et al. |
| 6,164,920 A | 12/2000 | Nazarian et al. |
| 6,241,945 B1 | 6/2001 | Owen |
| 6,267,926 B1 | 7/2001 | Reed et al. |
| 6,315,751 B1 | 11/2001 | Cosgrove et al. |
| 6,508,859 B1 | 1/2003 | Zia et al. |

OTHER PUBLICATIONS

Morita et al., "Closed Circuit Cardiopulmonary Bypass with Centrifugal Pump for Open–Heart Surgery: New Trial for Air Removal," *Artificial Organs* 24(6): 442–445 (2000).

Jorge Ojita, et al., "Assisted Venous Drainage Cardiopulmonary Bypass in Congenital Heart Surgery," Ann. Thorac. Surg., 71:1267–72(2001).

Joseph J. Sistino et al., "Laboratory Evaluation of a Low Prime Closed Circuit Cardiopulmonary Bypass System," J. Extra–Corp. Tech., 24(4):116–119 (1993).

Medtronic, "The BioPump Centrifugal Blood Pump" (1998).

Declaration of Jorge Ojito, Aug. 2003.

Declaration of Yehuda Tamari, Sep. 4, 2003.

BLOOD FILTER HAVING A SENSOR FOR ACTIVE GAS REMOVAL AND METHODS OF USE

REFERENCE TO RELATED APPLICATIONS

This application is a continuation-in-part of U.S. patent application Ser. No. 09/780,923, filed Feb. 9, 2001, the entirety of which is incorporated herein by reference.

FIELD OF THE INVENTION

The present invention relates to apparatus and methods for monitoring and removing air or other gases from the blood.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using a cardioplegia solution.

The development of minimally invasive techniques for cardiac bypass grafting, for example, by Heartport, Inc., Redwood City, Calif., and CardioThoracic Systems, Inc., Menlo Park, Calif., have placed a premium on reducing the size of equipment employed in the sterile field. Some previously known cardiopulmonary systems have attempted to miniaturize and integrate certain components of cardiopulmonary systems. U.S. Pat. Nos. 5,266,265 and 5,270,005, both to Raible, describe an extracorporeal blood oxygenation system having an integrated blood reservoir, an oxygenator formed from a static array of hollow fibers, a heat exchanger, a pump and a pump motor that is controlled by cable connected to a control console.

Concern over the entrainment of air in these, and conventional, blood handling systems led to the development of filtration designs with air venting capabilities. The placement of a filtration apparatus in the circuit as the final device to process the circulating blood before it is returned to the patient became the standard of care for cardiopulmonary bypass.

There exists a number of similar such filtration devices in clinical use. Many utilize a pleated element constructed of a woven fabric of a specified spacing to filter out particulate in a range of between 20 and 50 microns. U.S. Pat. No. 4,919,802 by Katsuri describes a pleated design that both filters and removes air from blood. Particulate matter of a size that exceeds the openings in the woven fabric is trapped and collected in the apparatus. The dimensions of the openings in the weave are subject to change, depending upon the amount of material and the pressure differential applied across the filter element.

The filter material of the Katsuri device is expected to deflect entrained air that is flowing tangential to the filter material, and to filter out bubbles that are greater in size than the filter material openings. The device includes a vent in its upper surface that enables air collected in the device to be vented to a venous reservoir. Because the venous reservoir typically operates at a lower pressure location in the circuit, flow from the vent location to the reservoir may be substantially continuous. Accordingly, air that enters the filtration apparatus is returned to, and ultimately vented from, the venous reservoir.

There are, however, a number of drawbacks attendant upon use of devices such as described in Katsuri. First, because the removal of air from the devices is through a vent either connected to a reservoir or alternative container, the pressure in the apparatus must be higher than the pressure in the reservoir or alternative container. Thus, it may be necessary to position the filter apparatus on the downstream, positive pressure side of a pump in a blood handling system. In addition, if the vent line is connected to a venous reservoir, a continuous flow of blood back to the reservoir is required to remove any air that may collect in the device. This return flow reduces or shunts the flow supplied to the patient and increases exposure of the blood to the foreign surfaces in the circuit. If a vacuum is applied to the open-air interface in the venous reservoir, the shunt flow is increased in proportion to the differential pressure.

Moreover, in most pleated designs, the pleated material forms a vertically oriented cylindrical tube that is potted at either end. The potting isolates the flow outside the pleated element from that inside of the pleated element. Air bubbles often become trapped underneath the upper potting, requiring the filter to be inverted to remove the bubbles, especially during the initial priming of the system.

In view of the limitations of previously known filtration systems, it would be desirable to provide a filter apparatus that monitors and removes gas for use, and methods of use, with an extracorporeal blood handling system.

It further would be desirable to provide a filter apparatus that monitors and removes gas, and methods of use, that permit one or more additional blood processing components, such as a heat exchanger, to be added to an extracorporeal blood circuit without having to prime the component prior to bringing that component online, thereby reducing disruption to operation of the blood handling system.

It also would be desirable to provide a filter apparatus that is capable of venting gas from the blood being processed without a shunt or loss of substantial blood from the flow supplied to the patient.

It still further would be desirable to provide a filter apparatus for monitoring and removing gas that can be disposed on the venous side of the extracorporeal circuit, either in conjunction with, or in place of, the venous reservoir.

SUMMARY OF THE INVENTION

In view of the foregoing, it is an object of the present invention to provide an apparatus and methods for filtering blood that monitors and removes air from an extracorporeal blood circuit to facilitate priming of the circuit and intraoperative use.

It is another object of the present invention to provide a filter apparatus that monitors and removes gas, and methods of uses, that permit one or more blood processing components, such as a heat exchanger, to be added to an extracorporeal blood circuit without having to prime the component prior to bringing that component online, thereby reducing disruption to operation of the blood handling system.

It is a further object of the present invention to provide a filter apparatus that is capable of venting gas from the blood being processed without a shunt or loss of substantial blood from the flow supplied to the patient.

It is yet another object of the present invention to provide a filter apparatus for monitoring and removing gas that can be disposed on the venous side of the extracorporeal circuit, either in conjunction with, or in place of, the venous reservoir.

These and other objects of the present invention are accomplished by providing a filter apparatus with a gas monitoring and removal system that removes air or other gases from the extracorporeal blood circuit. The apparatus of the present invention may be coupled to a conventional blood handling system, and may be initially primed with little or no saline or donor blood, with reduced risk of hemodilution. Moreover, additional components may be added to an existing extracorporeal circuit with little or no additional priming, and any air or other gases introduced into the system will be evacuated with no substantial impact on operation of a blood handling system.

In a preferred embodiment, a filter apparatus of the present invention monitors and removes gases from an extracorporeal blood circuit and comprises a housing having a gas collection plenum, a gas removal/blood filter, and a sensor positioned to sense gas within the interior of the housing to selectively remove gas. The gas removal/blood filter comprises a support structure that supports a screen-like material having an effective pore size between 20 and 250 microns. Alternatively, the gas removal/blood filter element may comprise a pleated filter material. Blood is introduced into the gas collection plenum via the blood inlet in a direction substantially tangential to the gas removal/blood filter to increase rotational velocity of the blood within the gas collection plenum, thereby enhancing separation of entrained gas.

Blood entering the housing via the blood inlet flows through the gas collection plenum, and air or other gases entrained in the blood are separated from the blood and collect in the gas collection plenum. A sensor disposed in communication with the gas collection plenum senses a parameter indicative of a level or volume of gas collected in the plenum, and selectively evacuates the plenum by coupling the plenum to a suction source, such as a standard operating room vacuum system. It is understood that if the placement of the filter apparatus is on the negative pressure side of the pump that the vacuum pressure must be regulated to be more negative than the pressure within the filter apparatus. Alternatively, if the filter apparatus is placed on the positive pressure side of the pump, the plenum may be simply connected to a container at atmospheric pressure. Blood that has been filtered exits the filter apparatus and passes to the rest of the blood handling system of the extracorporeal circuit.

Methods of operating the filter apparatus with the active gas removal system of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
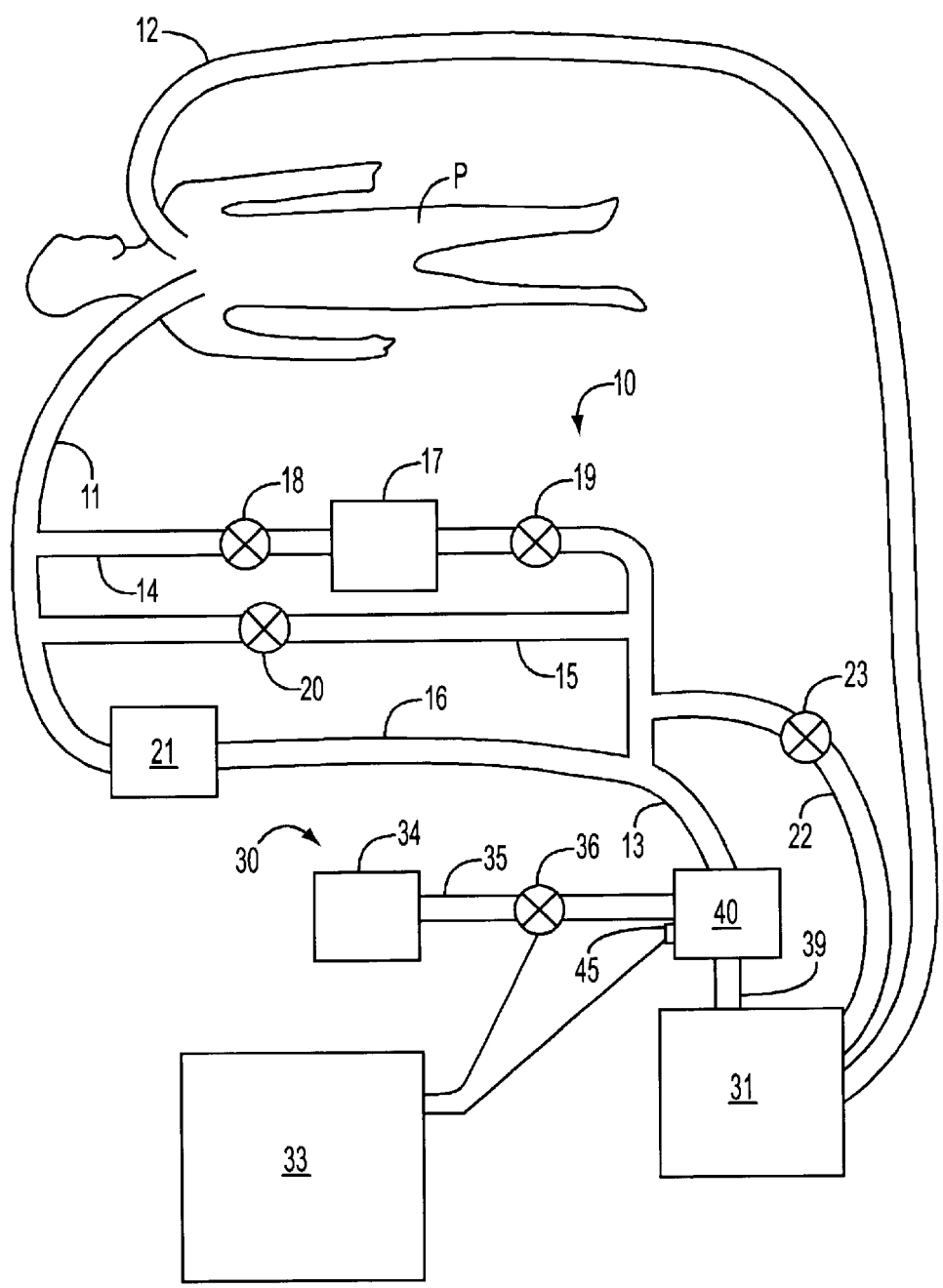
FIG. 1 is a schematic depiction of an extracorporeal blood circuit using the filter apparatus of the present invention.

Referring to FIG. 1, extracorporeal blood circuit 10, including filter apparatus 30 of the present invention, is described. In the description hereinafter, extracorporeal blood circuit 10 is designed for maintaining a patient on full or partial bypass support, for example, during a coronary artery bypass graft procedure or mitral valve repair procedure. Accordingly, conventional blood processing unit 31 may contain an extracorporeal blood oxygenation system having a blood reservoir, an oxygenator, a pump and a pump motor. Applicants note, however, that filter apparatus 30 is not limited to use in bypass support, but also may be used in any application that requires gas removal from fluids.

Extracorporeal blood circuit 10 includes venous line 11 that carries deoxygenated blood from patient P, and arterial line 12 that returns oxygenated blood to the patient. Each of venous line 11 and arterial line 12 are coupled to the patient through a suitable cannula, which is per se known. In accordance with known methods, the venous and arterial cannulae may be positioned in any suitable vein or artery.

Venous line 11 is coupled to inlet line 13 via lines 14, 15 and 16. Line 14 preferably includes dynamic reservoir 17 that can be selectively added and removed from the circuit using valves 18 and 19. Dynamic reservoir 17, which preferably is a flexible storage bag, permits blood to be stored or supplied as necessary. Valves 18 and 19 control blood flow into and out of dynamic reservoir 17. One advantage of this arrangement of extracorporeal blood circuit 10 is that a pump of the blood processing component 31 may be used to fill and evacuate the dynamic reservoir 17 during operation by simply manipulating valves 18 and 19. Alternatively, a conventional venous storage reservoir may be used instead of dynamic reservoir 17. The valves described in FIGS. 1–2 may range from conventional valves to manual clamps placed on tubing.

Line 15 includes valve 20 which may be activated to direct blood coming from the patient to either or both of lines 13 and 16. Line 16, which may include additional valving (not shown) permits additional blood processing unit 21, such as an additional filter or heat exchanger, to be included in extracorporeal blood circuit 10. Optional recirculation line 22 includes valve 23, and permits a portion of the output of blood processing component 31 to be recirculated to a point before gas removal element 40 in extracorporeal circuit 10, or used in administration of cardioplegia to the patient. Line 39 couples an output of gas removal element 40 of filter apparatus 30 to blood processing component 31.

Filter apparatus 30 includes sensor 45 and valve 36 adapted to be coupled to suction source 34 via line 35. Alternatively, if filter apparatus 30 is disposed on the positive pressure side of the pump, line 35 may be open to a container at atmospheric pressure. Valve 36 and sensor 45 preferably are electrically coupled to controller 33 so that controller 33 can regulate operation of valve 36 responsive to an output of sensor 45. As explained in greater detail hereinafter, the filter apparatus of the present invention automatically removes air and other gases from extracorporeal blood circuit 10 and blood processing component 31 during priming and operation of the bypass system.

Figure 2A:
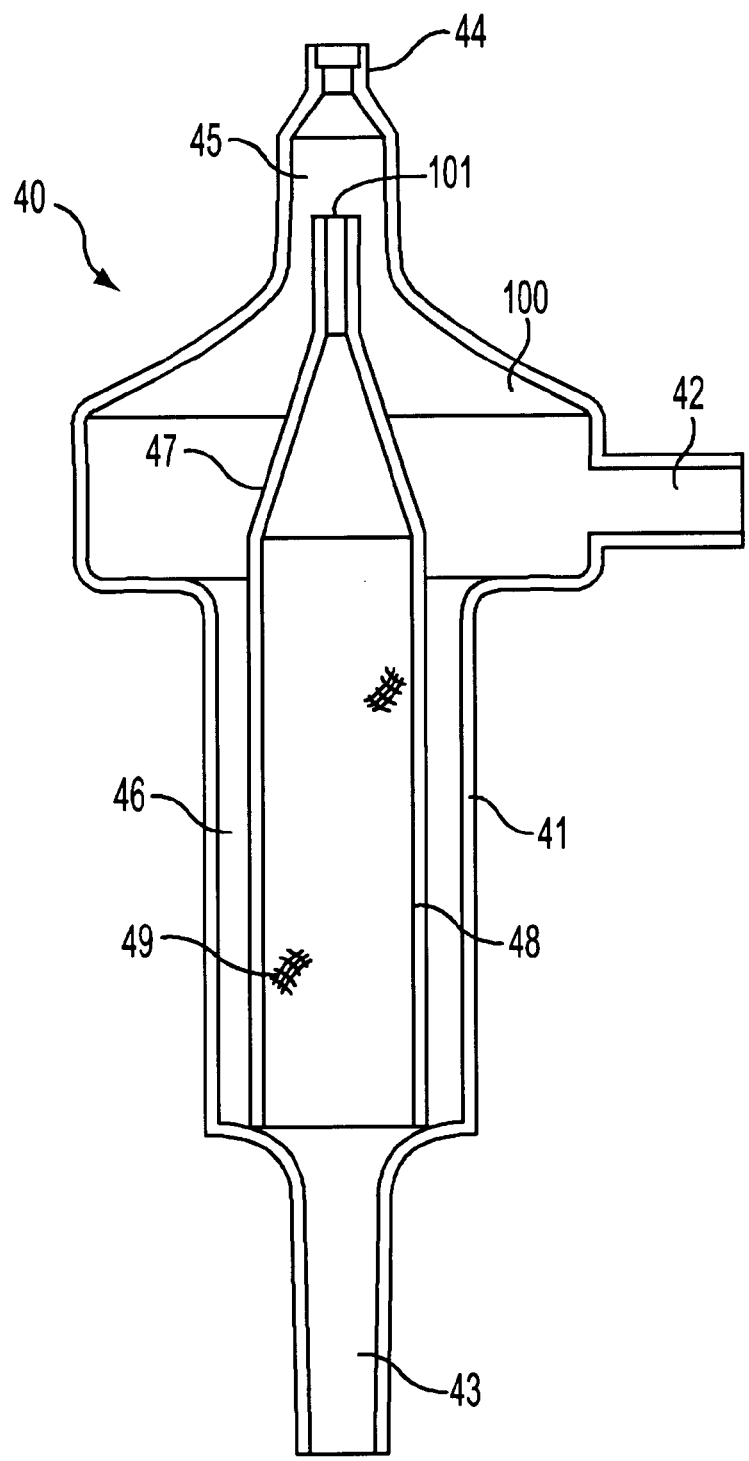
FIGS. 2A and 2B are, respectively, cross-sectional views of a gas removal/blood filter of the filter apparatus of the present invention.
Figure 2B:
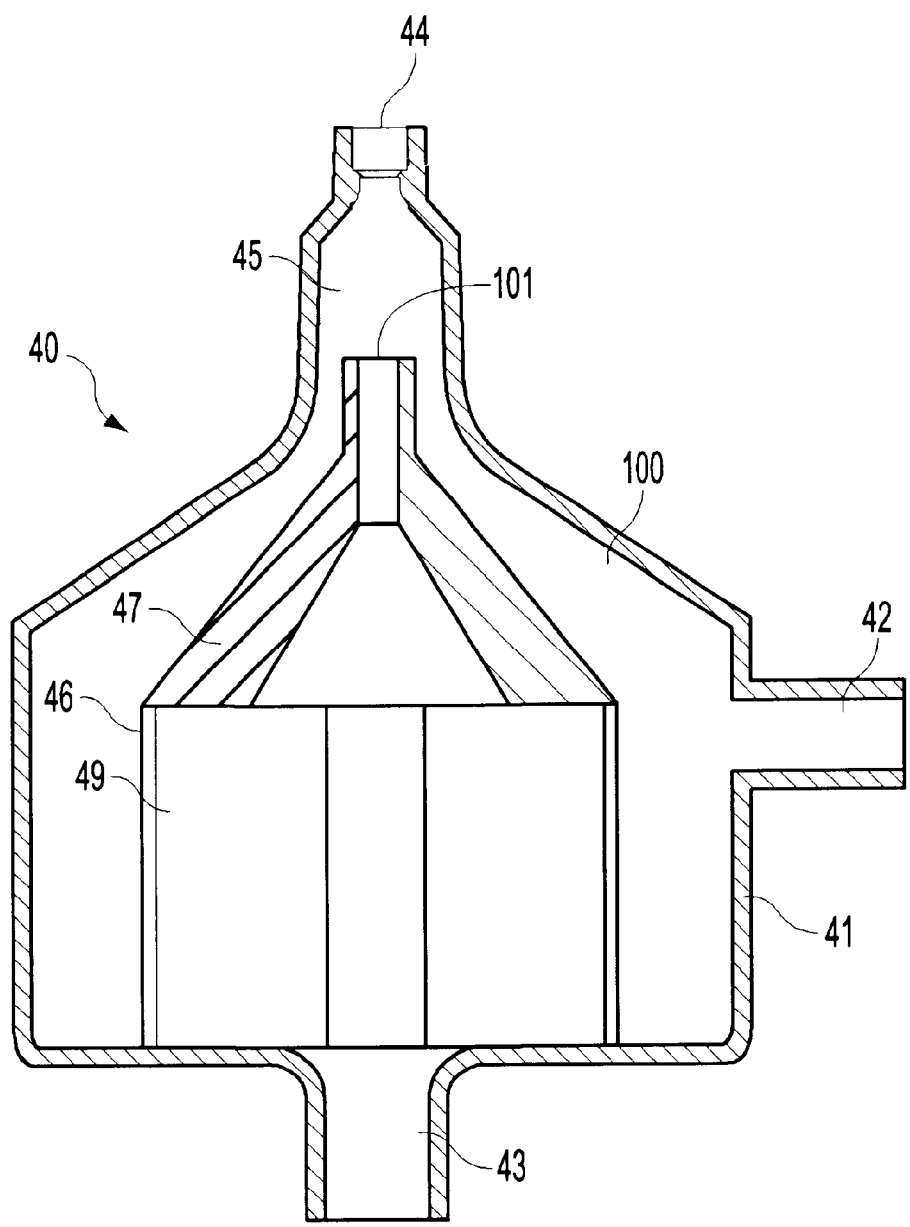

Referring now to FIG. 2A, gas removal element 40 in accordance with the present invention is described. Gas removal element 40 is intended for use with previously known extracorporeal bypass systems. Gas removal element 40 includes transparent housing 41 having blood inlet 42, blood outlet 43, gas removal port 44, and gas collection plenum 100. Housing 41 encloses gas removal/blood filter 46, which in turn comprises generally conical upper wall 47, support structure 48 and filter material 49. Support structure 48 is not required if filter material 49 is self supporting. Upper wall 47, support structure 48 and filter material 49 may be constructed as described with respect to the embodiments of FIG. 3 or 4 set forth hereinafter. FIG. 2B is an alternative gas removal/blood filter element of the filter apparatus of the present invention in which filter element 46 is positioned entirely in gas collection plenum 100.

Gas removal/blood filter 46 causes gas entrained in blood introduced into gas collection plenum 100 to separate and collect in the upper portions of gas collection plenum 100. Blood inlet 42 is displaced tangentially relative to the centerline of housing 41, so that blood passing through blood inlet 42 into gas collection plenum 100 swirls around upper wall 47, which is preferably fluid impermeable.

Upper wall 47 also preferably includes a chamber having a central opening 101 through its upper surface, which communicates with the upper portion of gas collection plenum 100. This configuration allows any gas that passes through filter material 49 to escape through opening 101 and be evacuated from gas collection plenum 100. Advantageously, this feature facilitates rapid and easy priming of blood processing component 31, as described hereinafter.

Filter material 49 comprises one or multiple layers of a screen-like material having an effective pore size of between 20 and 250 microns, and is mounted to baffled support structure 48. Filter material 49 serves to exclude bubbles from the blood flow by maintaining the swirling action of the blood for a sufficient time to allow the bubbles to rise to the gas collection plenum. Because the blood circulates around the outside of gas removal/blood filter 46, bubbles impinge against filter material 49 tangentially, and thus "bounce off." Filter material 49 also filters out particulate matter.

Figure 3A:
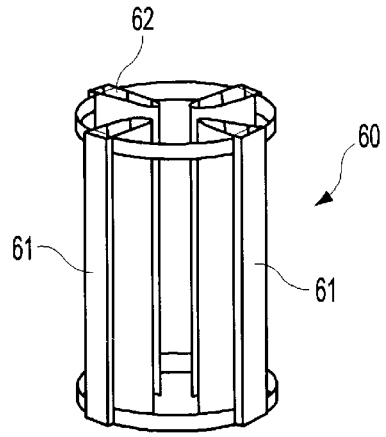
FIGS. 3A and 3B are, perspective and cross-sectional views of a gas removal/blood filter element of the filter apparatus of the present invention.
Figure 3B:
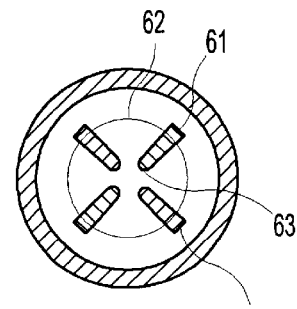
Figure 4A:
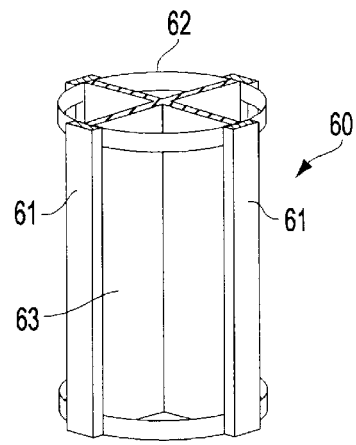
FIGS. 4A and 4B are, respectively, perspective and cross-sectional views of a first alternative gas removal/blood filter element of the filter apparatus of the present invention.
Figure 4B:
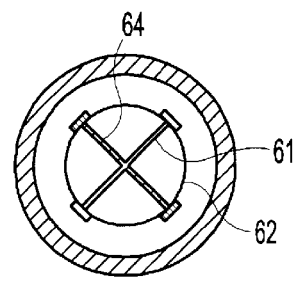

As illustrated in FIGS. 3A and 3B, support structure 48 forms an open cage 60 having longitudinal struts 61 and support rings 62. Struts 61 extend radially inward and preferably include radiused inner ends 63. Struts 61 serve as baffles to reduce swirling of blood that has passed through filter material 49. In an alternative embodiment, shown in FIGS. 4A and 4B, struts 61 are further extended radially inward to form fluid impermeable cruciform structure 64.

Figure 5A:
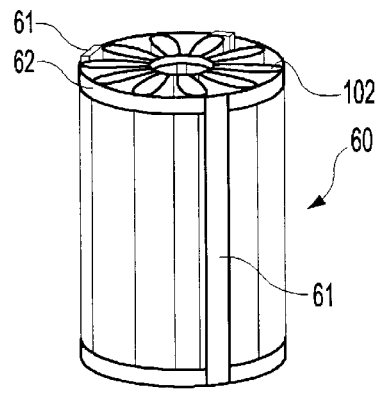
FIGS. 5A and 5B are, respectively, perspective and cross-sectional views of a second alternative gas removal/blood filter element of the filter apparatus of the present invention.
Figure 5B:
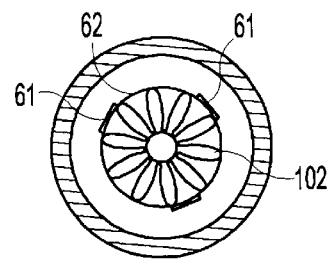

Rather than a screen-like filter material, gas removal/blood filter 46 may comprise a pleated structure 102, as depicted in FIGS. 5A and 5B. In most pleated designs, the potting at the top of the filter element forms a closed conical feature that is intended to facilitate rotational flow above the pleated element to concentrate air separated from blood to the vent location. The potting, however, also serves to isolate the flow outside the pleated element from that inside the pleated element. During priming, bubbles may become trapped underneath the upper potting compound, requiring the filter to be inverted and to dislodge the bubbles. To address this problem, the present invention includes central opening 101 as described hereinabove. Previously, it was thought that filters of such design would allow a shunt path to exist around the filter element such that during use the flow would bypass the filter and reduce the filtration efficiency.

However, the velocity of blood flow in upper plenum 100 around upper wall 47 is higher than the flow velocity at central opening 101. This creates a pressure differential such that the flow does not bypass filter 46. Rather, a small amount of blood flows through central opening 101 from the inner core of the gas removal/blood filter 46 after having traversed through filter material 49. The flow then merges with blood in gas collection plenum 100 and is recirculated back to gas removal/blood filter 46. The recirculation flow increases the potential for gas that had not been previously removed by pleated filter 102, or alternatively screen-like filter material 49, to be removed when the recirculation flow retraverses gas collection plenum 100 and gas removal/blood filter 46. The ability to remove gas from gas removal/blood filter 46 in this manner eliminates the need to invert the filter during priming, as is required for previously known designs.

In accordance with the present invention, filter apparatus 30 includes sensor 45 that monitors the level of gas or blood in gas collection plenum 100. Sensor 45 may sense a parameter indicative of a level or volume of air or other gas in gas collection plenum 100, or may simply detect the absence of blood, and may be any suitable sensor that preferably operates by a non-contact method. Suitable sensor methods include electrical-charge based, optical and acoustic methods. A resistive contact method also could be employed, in which a low electrical current is passed between adjacent electrodes only in the presence of blood.

Sensor 45 preferably is of a capacitance type, per se known in the art, that detects a change in electrical capacitance between the bulk of a liquid (in this case, blood or saline) and gas. Alternatively, sensor 45 may be optical in nature, and use a light source that has a wavelength that is minimally attenuated by blood. In this case, the light source is directed, at an oblique angle, through the blood at the top of the gas collection plenum towards a photodetector, and the sensor is positioned to detect the change in the refractive index of the blood (or saline prime) caused by the presence of air or other gases. In another alternative embodiment, sensor 45 may use an ultrasonic energy source and receiver to detect the presence of gas or absence of blood by the change in acoustic transmission characteristics.

In accordance with the present invention, filter apparatus 30 also includes valve 36 that couples suction source 34 to gas removal element 40. Valve 36 is preferably a solenoid-controlled one-way valve. The uni-directional characteristic of the valve prevents air from entering the filter apparatus if the vacuum should stop and the valve should remain open, of course, one skilled in the art will recognize that an alternative valve that is electrically controlled or actuated may also be used.

In operation, deoxygenated blood from patient P is routed through one or more lines 14–16 to blood inlet 42 of gas removal element 40. Blood entering gas collection plenum 100 is induced to circulate around the exterior of upper wall 47 and gas removal/blood filter 46 until air or other gases entrapped in the blood separate out of the blood and collect in the upper portion of gas collection plenum 100. Responsive to the detection of the presence of a predetermined level or volume of gas by sensor 45, controller 33 controls operation of valve 36 to evacuate the gas. Specifically, the output of sensor 45 is supplied to controller 33 of filter apparatus 30 (see FIG. 1), which in turn regulates valve 36. When sensor 45 outputs a signal indicating that gas is present in gas collection plenum 100, controller 33 opens valve 36, thereby coupling gas collection plenum 100 to suction source 34, such as a vacuum bottle, pump or standard operating room suction port, to evacuate the gas. Once the gas is evacuated, and the sensor detects blood at an appropriate level in gas collection plenum 100, the sensor changes its output. Correspondingly, controller 33 then closes valve 36. In this manner, gas is continuously monitored and then automatically removed from the blood by filter apparatus 30. As will be understood by one of ordinary skill in the art, controller 33 may be a preprogrammed microprocessor or may comprise an ASIC, while valve 36 may be coupled to a solenoid that is operable responsive to the signal generated by controller 33.

Importantly, suction source 34 is only necessary if filter apparatus 30 is placed prior to blood processing unit 31 on the venous side of extracorporeal circuit 10. If filter apparatus 30 is placed after unit 31 on the arterial side of circuit 10, the pressure of the pump within blood processing unit 31 provides the driving force to remove gases from gas removal element 40. Without a suction source, the air level would still be monitored with sensor 45 but air could be bled off into the atmosphere as it accumulates by opening valve 36. Of course, a suction source could still be used even if filter apparatus 30 is placed on the arterial side of circuit 10.

The filter apparatus with active gas removal of the present invention provides a number of advantages. First, the system facilitates priming of a conventional blood handling system with significantly less saline or donor blood. As is conventional, before initiating bypass support, the entire extracorporeal blood circuit must be primed with blood to purge all air. Applicants have observed in prototype designs that the filter apparatus of the present invention is capable of removing large amounts of air from the extracorporeal blood circuit during initial startup, thereby greatly reducing the amount of time and/or manipulation typically required for priming. In addition, controller 33 may be actuated without the presence of air to displace priming solution, such as saline or donor blood, with the patient's blood thus reducing the volume of priming solution returned to the patient. Advantageously, this feature facilitates rapid and easy set-up of the blood handling system, as well as reduces the amount of priming solution delivered to the patient.

Moreover, when priming the extracorporeal blood circuit, the patient's own blood pressure may be used to fill venous lines 11, 14–16 and blood processing component 31. Advantageously, the filter apparatus may be used to actively remove air and draw blood into extracorporeal circuit 10. In particular, when the filter apparatus is turned on, sensor 45 will detect gas in the gas collection plenum 100 and will then actively remove the gas as described hereinabove. In this manner, extracorporeal circuit 10 can be primed by operation of the filter apparatus with active gas removal. Once extracorporeal circuit 10 has been thus primed, a pump in blood processing component 31 may be operated together with the filter apparatus to purge air from the circuit. Blood may be recirculated through line 22 and valve 23 until all air has been purged from the extracorporeal circuit.

Another advantage of the system of the present invention is that additional blood processing element 21 may be added to the extracorporeal circuit during operation, with the filter apparatus priming the newly added device during operation. When such an element 21 is added to the circuit during operation, line 16 is temporarily clamped to isolate the location for new element 21. Blood processing element 21 then is connected, potentially unprimed, in line 16. The clamps then are opened, so that any air in new element 21 is removed automatically by the filter apparatus. The filter apparatus of the present invention therefore may be used to remove air while the blood handling system is delivering blood to the patient or when simply circulating the blood through line 22 until it is confirmed that all air from new element 21 has been removed.

Yet another advantage of the present invention is the elimination of the need to place a gas removal apparatus downstream of a high pressure source, such as a pump. By use of a suction source, the present system eliminates the requirement that the pressure in the gas removal element be at a higher pressure than that of the reservoir to which the gas escapes, thereby eliminating the need for a venous reservoir. Accordingly, the filter apparatus may be placed on the venous side of an extracorporeal circuit prior to a blood processing unit, rather than being placed immediately before the return of the processed blood back to the patient.

Although preferred illustrative embodiments of the present invention are described above, it will be evident to one skilled in the art that various changes and modifications may be made without departing from the invention. It will also be evident that the filter apparatus with active gas removal can be coupled with one or more blood processing elements, such as a pump and oxygenator as described and/or a heat exchanger. It will further be evident that the filter apparatus with active gas removal can be used for applications other than cardiac surgery. The filter apparatus may be used for any application that requires the removal of gas and particulate matter from a liquid. It is intended in the appended claims to cover all such changes and modifications that fall within the true spirit and scope of the invention.

What is claimed is:

1. A filter apparatus for removing gas from blood, comprising:
    a housing having an interior, a gas removal port, a blood inlet, a blood outlet, and an upper surface defining an apex, the gas removal port located at the apex of the housing;
    a sensor positioned to sense gas within the interior of the housing; and
    a filter element disposed within the interior of the housing, the filter element having a fluid impermeable conical upper wall around which fluid circulates upon entry into the housing, the conical upper wall defining a central opening allowing communication the interior of the filter element and the gas removal port.

2. The apparatus of claim 1, wherein the filter, element comprises filter material.

3. The apparatus of claim 2, wherein the filter material is screen-like and comprises at least one layer.

4. The apparatus of claim 3, wherein the filter element rises an open cage that supports the screen like material.

5. The apparatus of claim 3, wherein the filter element further comprises a fluid impermeable cruciform structure that supports the screen-like material.

6. The apparatus of claim 2, wherein the filter material has effective pore size between 20 to 250 microns.

7. The apparatus of claim 1, wherein the filter element is disposed within the housing to separate the inlet from the outlet so that blood entering the inlet must pass through the filter element.

8. The apparatus of claim 1, wherein the filter element filters out particulate matter.

9. The apparatus of claim 1, wherein the filter element comprises a pleated material.

10. The apparatus of claim 1, wherein the sensor either senses a parameter indicative of a level or volume of gas collected in the housing.

11. The apparatus of claim 1, wherein the sensor uses a sensing technique selected from the group consisting of: detecting by capacitance, direct resistance, light absorbance, light refractance, and ultrasonic energy transmittance.

12. The apparatus of claim 1, further comprising a valve operably coupled to the sensor, the valve opening responsive to detection of gas by the sensor.

13. The apparatus of claim 12, further comprising a controller that controls operation of the valve responsive to a signal provided by the sensor.

14. The apparatus of claim 1, further comprising a one-way valve that prevents air from flowing into the filter apparatus.

15. The apparatus of claim 1, further comprising at least one baffle disposed within the filter element.

16. The apparatus of claim 1, wherein the inlet directs the blood in a substantially tangential direction so that blood initially circulates within the interior.

17. The apparatus of claim 1, wherein the sensor detects the absence of blood.

18. A filter apparatus for removing gas from blood, comprising:
- a housing having an interior, a gas removal port, a blood inlet, a blood outlet, and an upper surface defining an apex, the gas removal port located at the apex of the housing;
- a sensor positioned to sense gas within the interior of the housing; and
  - a filter element disposed within the interior of the housing, the filter element having a fluid impermeable upper wall around which fluid circulates upon entry into the housing, the upper wall defining a central opening allowing communication between the interior of the filter element and the gas removal port,
- wherein the blood inlet directs blood in a substantially tangential direction so that blood initially circulates around the upper wall upon entering the interior of the housing.

19. The apparatus of claim 18, further comprising a valve operably coupled to the sensor, the valve opening responsive to detection of gas by the sensor.

20. The apparatus of claim 19, further comprising a controller that controls operation of the valve responsive to a signal provided by the sensor.

21. The apparatus of claim 18, wherein the filter element comprises filter material.

22. The apparatus of claim 21, wherein the filter material is screen-like and comprises at least one layer.

23. The apparatus of claim 21, wherein the filter material has effective pore size between 20 to 250 microns.

24. The apparatus of claim 18, wherein the filter element is disposed within the housing to separate the inlet from the outlet so that blood entering the inlet must pass through the filter element.

25. The apparatus of claim 24, wherein the filter element further comprises an open cage that supports the screen-like material.

26. The apparatus of claim 24, wherein the filter element further comprises a fluid impermeable cruciform structure that supports the screen-like material.

27. The apparatus of claim 18, wherein the filter element filters out particulate matter.

28. The apparatus of claim 18, wherein the filter element comprises a pleated material.

29. The apparatus of claim 18, wherein the sensor either senses a parameter indicative of a level or volume of gas collected in the housing.

30. The apparatus of claim 18, wherein the sensor uses a sensing technique selected from the group consisting of: detection by capacitance, direct resistance, light absorbance, light refractance, and ultrasonic energy transmittance.

31. The apparatus of claim 18, further comprising a one-way valve that prevents air from flowing into the filter apparatus.

32. The apparatus of claim 18, further comprising at least one baffle disposed within the filter element.

33. The apparatus of claim 18, wherein the sensor detects the absence of blood.

34. The apparatus of claim 18, wherein the upper wall has a conical configuration.

* * * * *